United States Patent [19]

Wallace

[11] Patent Number: 5,417,959
[45] Date of Patent: May 23, 1995

[54] FUNCTIONALIZED AZA-CRYTAND LIGANDS FOR DIAGNOSTIC IMAGING APPLICATIONS

[75] Inventor: Rebecca A. Wallace, Manchester, Mo.

[73] Assignee: Mallinckrodt Medical, Inc., St. Louis, Mo.

[21] Appl. No.: 130,618

[22] Filed: Oct. 4, 1993

[51] Int. Cl.⁶ .................. A61B 5/055; C07D 225/00; C07D 245/00
[52] U.S. Cl. .................. 424/9.363; 424/1.65; 424/1.77; 424/9.42; 534/15; 534/16; 540/465; 540/472; 128/653.4; 514/183; 514/186; 514/431; 514/450; 436/173
[58] Field of Search ............ 424/9, 4, 1.65, 1.77; 534/15, 16; 540/465, 472; 436/173; 128/653.4, 654; 514/186, 431, 450, 183

[56] References Cited

U.S. PATENT DOCUMENTS

| | | | |
|---|---|---|---|
| 3,531,468 | 9/1970 | Park et al. | 540/472 |
| 4,927,923 | 5/1990 | Mathis et al. | 540/456 |
| 5,322,681 | 6/1994 | Klaveness | 424/9 |

FOREIGN PATENT DOCUMENTS 0438206 1/1991 European Pat. Off. .

*Primary Examiner*—Gary E. Hollinden
*Attorney, Agent, or Firm*—Brian K. Stierwalt

[57] ABSTRACT

The present invention provides new and structurally diverse compositions comprising compounds of the general formula:

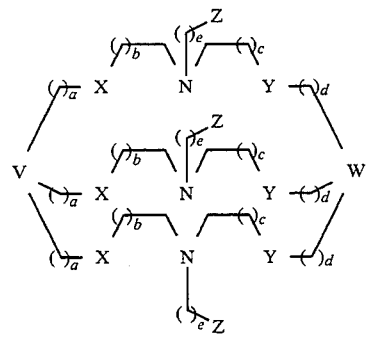

Wherein V is $CR_1$ or N; W is $CR_2$ or N; $R_1$ and $R_2$ may be the same or different and are hydrogen, $C_1$-$C_8$ alkyl, or $C_6$-$C_{10}$ aryl, optionally $R_1$ and $R_2$ may be substituted by one or more hydroxy, $C_1$-$C_8$ alkyl, $C_1$-$C_8$ hydroxyalkyl, $C_1$-$C_8$ alkoxy, $C_6$-$C_{10}$ aryl, $C_6$-$C_{10}$ hydroxyaryl, $C_6$-$C_{10}$ aryloxy, $-CO_2R_3$, $CONR_4R_5$, or $-NR_4R_5$; X and Y may be the same or different and the O, $NR_6$, S, or $CR_7R_8$; $R_3$, $R_4$, $R_5$, $R_6$, $R_7$ and $R_8$ may be the same or different and are hydrogen, $C_1$-$C_8$ alkyl, $C_1$-$C_8$ hydroxyalkyl, or $C_1$-$C_8$ alkoxyalkyl; $R_4$ and $R_5$ may form a 5 or 6 membered carbocyclic ring optionally containing singularly or in combination nitrogen, oxygen or sulfur; a, b, c, d and e may be same or different and are zero to about 10; and Z is $-CO_2H$, $-PO_3H_2$, $-SO_3H$, or $-CONHOH$.

Methods for imaging using compositions of the invention as diagnostic imaging agents are also provided.

12 Claims, No Drawings

FUNCTIONALIZED AZA-CRYTAND LIGANDS FOR DIAGNOSTIC IMAGING APPLICATIONS

FIELD OF THE INVENTION

This invention relates to magnetic resonance imaging (MRI), x-ray imaging, and radiopharmaceuticals. More particularly the invention relates to methods and compositions for enhancing MRI, x-ray imaging, and radiopharmaceuticals.

BACKGROUND OF THE INVENTION

The use of contrast agents in diagnostic medicine is rapidly growing. In X-ray diagnostics, for example, increased contrast of internal organs, such as the kidneys, the urinary tract, the digestive tract, the vascular system of the heart (angiography), and so forth is obtained by administering a contrast agent which is substantially radiopaque. In conventional proton MRI diagnostics, increased contrast of internal organs and tissues may be obtained by administering compositions containing paramagnetic metal species which increase the relaxivity of surrounding protons. In ultrasound diagnostics, improved contrast is obtained by administering compositions having acoustic impedances different than that of blood and other tissues.

The recently developed technique of MRI encompasses the detection of certain atomic nuclei utilizing magnetic fields and radio-frequency radiation. It is similar in some respects to X-ray computed tomography (CT) in providing a cross-sectional display of the body organ anatomy with excellent resolution of soft tissue detail. As currently used, the images produced constitute a map of the proton density distribution, the relaxation times, or both, in organs and tissues. The technique of MRI is advantageously non-invasive as it avoids the use of ionizing radiation.

While the phenomenon of NMR was discovered in 1945, it is only recently that it has found application as a means of mapping the internal structure of the body as a result of the original suggestion of Lauterbur (*Nature*, 242, 190–191 [1973]). The fundamental lack of any known hazard associated with the level of the magnetic and radio-frequency fields that are employed renders it possible to make repeated scans on vulnerable individuals. In addition to standard scan planes (axial, coronal, and sagittal), oblique scan planes can also be selected.

With an MRI experiment, the nuclei under study in a sample (e.g. protons) are irradiated with the appropriate radio-frequency (RF) energy in a highly uniform magnetic field. These nuclei, as they relax, subsequently emit RF at a sharp resonance frequency. The resonance frequency of the nuclei depends on the applied magnetic field.

According to known principles, nuclei with appropriate spin, when placed in an applied magnetic field (B, expressed generally in units of gauss or Tesla [$10^4$ gauss]) align in the direction of the field. In the case of protons, these nuclei precess at a frequency, f, of 42.6 MHz, at a field strength of 1 Tesla. At this frequency, an RF pulse of radiation will excite the nuclei and can be considered to tip the net magnetization out of the field direction, the extent of this rotation being determined by the pulse duration and energy. After the RF pulse, the nuclei "relax" or return to equilibrium with the magnetic field, emitting radiation at the resonant frequency. The decay of the emitted radiation is characterized by two relaxation times, i.e., $T_1$, the spin-lattice relaxation time or longitudinal relaxation time, that is, the time taken by the nuclei to return to equilibrium along the direction of the externally applied magnetic field, and $T_2$, the spin-spin relaxation time associated with the dephasing of the initially coherent precession of individual proton spins. These relaxation times have been established for various fluids, organs and tissues in different species of mammals.

In MRI, scanning planes and slice thicknesses can be selected. This selection permits high quality transverse, coronal and sagittal images to be obtained directly. The absence of any moving parts in MRI equipment promotes high reliability. It is believed that MRI has a greater potential than CT for the selective examination of tissue characteristics in view of the fact that in CT, X-ray attenuation coefficients alone determine image contrast, whereas at least five separate variables ($T_1$, $T_2$, proton density, pulse sequence and flow) may contribute to the MRI signal.

By reason of its sensitivity to subtle physicochemical differences between organs and/or tissues, it is believed that MRI may be capable of differentiating different tissue types and in detecting diseases which induce physicochemical changes that may not be detected by X-ray or CT which are only sensitive to differences in the electron density of tissue.

As noted above, two of the principal imaging parameters are the relaxation times, $T_1$ and $T_2$. For protons (or other appropriate nuclei), these relaxation times are influenced by the environment of the nuclei, (e.g., viscosity, temperature, and the like). These two relaxation phenomena are essentially mechanisms whereby the initially imparted radio-frequency energy is dissipated to the surrounding environment. The rate of this energy loss or relaxation can be influenced by certain other nuclei which are paramagnetic. Chemical compounds incorporating these paramagnetic nuclei may substantially alter the $T_1$ and $T_2$ values for nearby protons. The extent of the paramagnetic effect of a given chemical compound is a function of the environment.

In general, paramagnetic species such as ions of elements with atomic numbers of 21 to 29, 42 to 44 and 58 to 70 have been found effective as MRI image contrasting agents. Examples of suitable ions include chromium(III), manganese(II), manganese(III), iron(II), iron(III), cobalt(II), nickel(II), copper(II), praseodymium(III), neodymium(III), samarium(III), and ytterbium(III). Because of their very strong magnetic moments, gadolinium(III), terbium(III), dysprosium(III), holmium(III) and erbium(III) are preferred. Gadolinium(III) ions have been particularly preferred as MRI contrasting agents.

Typically, paramagnetic ions have been administered in the form of complexes with organic complexing agents. Such complexes provide the paramagnetic ions in a soluble, nontoxic form, and facilitate their rapid clearence from the body following the imaging procedure. Gries et al., U.S. Pat. No. 4,647,447, disclose complexes of various paramagnetic ions with conventional aminocarboxylic acid complexing agents. A preferred complex disclosed by Gries et al. is the complex of gadolinium(III) with diethylenetriamine-pentaacetic acid ("DTPA").

Paramagnetic ions, such as gadolinium(III), have been found to form strong complexes with DTPA, ethylenediamine-tetraacetic acid ("EDTA"), and with tetraazacyclododecane-N,N',N'',N'''-tetraacetic acid ("DOTA").

These complexes do not dissociate substantially in physiological aqueous fluids. The gadolinium complex of DTPA has a net charge of −2, whereas the gadolinium complex of EDTA or DOTA has a net charge of −1, and both are generally administered as soluble salts. Typical salts are sodium and N-methylglucamine. The administration of salts is attended by certain disadvantages. These salts can raise the in vivo ion concentration and cause localized disturbances in osmolality, which in turn, can lead to edema and other undesirable reactions.

Efforts have been made to design new ionic and neutral paramagnetic metal complexes which avoid or minimize the above mentioned disadvantages. In general, this goal can be achieved by converting one or more of the free carboxylic acid groups of the complexing agent to neutral, non-ionizable groups. For example, S.C. Quay, in U.S. Pat. Nos. 4,687,658 and 4,687,659, discloses alkylester and alkylamide derivatives, respectively, of DTPA complexes. Similarly, published Dean et al., U.S. Pat. No. 4,826,673 discloses mono- and polyhydroxyalkylamide derivatives of DTPA and their use as complexing agents for paramagnetic ions. It can also be achieved by covalent attachment of organic cations to the complexing agent in such a manner that the sum of positive and negative charges in the resulting metal complex is zero.

The nature of additional substituents in the complexing agent can have a significant impact on tissue specificity. Hydrophilic complexes tend to concentrate in the interstitial fluids, whereas lipophilic complexes tend to associate with cells. Thus, differences in hydrophilicity can lead to different applications of the compounds. See, for example, Weinmann et al., AJR, 142, 679 (Mar. 1984) and Brasch, et al., AJR, 142, 625 (Mar. 1984).

Finally, toxicity of paramagnetic metal complexes is greatly affected by the nature of the complexing agents. In vivo release of free metal ions from the complex is a major cause of toxicity. Four principal factors are important in the design of chelates for making paramagnetic metal complexes that are highly stable in vivo and less toxic. The first three factors are thermodynamic in nature whereas the fourth involves chelate kinetics. The first factor is the thermodynamic stability constant of the metal-ligand. The thermodynamic stability constant indicates the affinity that the totally unprotonated ligand has for a metal. The second factor is the conditional stability constant which takes into account the pH and is important when considering stability under physiological pH. The selectivity of the ligand for the paramagnetic metal over other endogenous metal ions such as zinc, iron, magnesium and calcium is the third factor. In addition to the three thermodynamic considerations, complexes with structural features that make in vivo transmetallation reactions much slower than their clearance rates would be predicted to have low toxicities. Therefore, in vivo reaction kinetics are a major factor in the design of stable complexes. See, for example, Cacheris et al., Magnetic Resonance Imaging, 8:467 (1990) and Oksendal, et al., JMRI, 3:157 (1993).

A need continues to exist for new and structurally diverse compounds for use as imaging agents and radiopharmaceuticals. There is a further need to develop highly stable complexes with good relaxivity and osmolar characteristics.

SUMMARY OF THE INVENTION

The present invention provides new and structurally diverse compositions comprising compounds of the general formula:

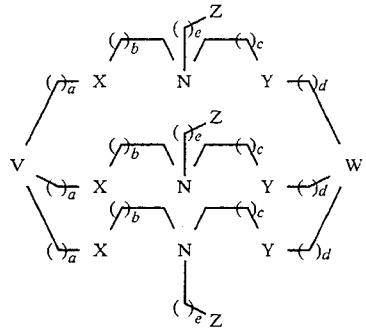

Wherein V is $CR_1$ or N; W is $CR_2$ or N; $R_1$ and $R_2$ may be the same or different and are hydrogen, $C_1$–$C_8$ alkyl, or $C_6$–$C_{10}$ aryl, optionally $R_1$ and $R_2$ may be substituted by one or more hydroxy, $C_1$–$C_8$ alkyl, $C_1$–$C_8$ hydroxyalkyl, $C_1$–$C_8$ alkoxy, $C_6$–$C_{10}$ aryl, $C_6$–$C_{10}$ hydroxyaryl, $C_6$–$C_{10}$ aryloxy, —$CO_2R_3$, $CONR_4R_5$, or —$NR_4R_5$; X and Y may be the same or different and the O, $NR_6$, S, or $CR_7R_8$; $R_3$, $R_4$, $R_5$, $R_6$, $R_7$ and $R_8$ may be the same or different and are hydrogen, $C_1$–$C_8$ alkyl, $C_1$–$C_8$ hydroxyalkyl, or $C_1$–$C_8$ alkoxyalkyl; $R_4$ and $R_5$ may form a 5 or 6 membered carbocyclic ring optionally containing singularly or in combination nitrogen, oxygen or sulfur; a, b, c, d and e may be same or different and are zero to about 10; and Z is —$CO_2H$, —$PO_3H_2$, —$SO_3H$, or —$CONHOH$.

Also provided are compositions comprising complexes of the compounds with metal ions of the general formula:

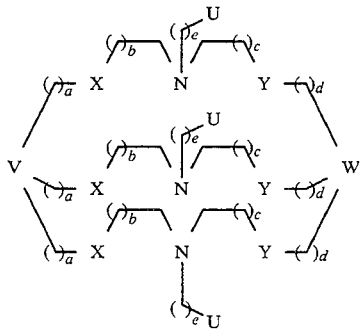

Wherein V is $CR_1$ or N; W is $CR_2$ or N; $R_1$ and $R_2$ may be the same or different and are hydrogen, $C_1$–$C_8$ alkyl, or $C_6$–$C_{10}$ aryl, optionally $R_1$ and $R_2$ may be substituted by one or more hydroxy, $C_1$–$C_8$ alkyl, $C_1$–$C_8$ hydroxyalkyl, $C_1$–$C_8$ alkoxy, $C_6$–$C_{10}$ aryl, $C_6$–$C_{10}$ hydroxyaryl, $C_6$–$C_{10}$ aryloxy, —$CO_2R_3$, $CONR_4R_5$, or —$NR_4R_5$; X and Y may be the same or different and the O, $NR_6$, S, or $CR_7R_8$; $R_3$, $R_4$, $R_5$, $R_6$, $R_7$ and $R_8$ may be the same or different and are hydrogen, $C_1$–$C_8$ alkyl, $C_1$–$C_8$ hydroxyalkyl, or $C_1$–$C_8$ alkoxyalkyl; $R_4$ and $R_5$ may form a 5 or 6 membered carbocyclic ring optionally containing singularly or in combination nitrogen, oxygen or sulfur; a, b, c, d and e may be same or different and are zero to about 10; U is —$CO_2M$, —$PO_3HM$, —$SO_3M$ or $CONHOM$; and M is a metal ion or equivalent and/or a physiologically acceptable cation of an inorganic or organic base.

Compositions comprising the above formulas wherein M is a radioactive metal ion, a paramagnetic ion, or a metal ion capable of absorbing x-rays are also provided for use as radiopharmaceuticals, magnetic resonance imaging, and x-ray contrast agents, respectively.

Diagnostic compositions comprising the compounds of the invention are also provided. Methods of performing diagnostic procedures with compositions of the invention are also disclosed. The methods comprise administering to a patient an effective amount of the compositions of the invention and optionally subjecting the patient to an imaging procedure of imaging.

DETAILED DESCRIPTION

The compositions of the invention are suitable for use with a variety of modalities including x-rays, magnetic resonance imaging and radiopharmaceuticals.

The functionality of the R groups of the compositions of the invention afford the additional capability of derivatization to biomolecules and synthetic polymers. Biomolecule refers to all natural and synthetic molecules that play a role in biological systems. Biomolecules include hormones, amino acids, peptides, peptidomimetics, proteins, deoxyribonucleic acid (DNA) ribonucleic acid (RNA), lipids, albumins, polyclonal antibodies, receptor molecules, receptor binding molecules, monoclonal antibodies and aptamers. Specific examples of biomolecules include insulins, prostaglandins, growth factors, liposomes and nucleic acid probes. Examples of synthetic polymers include polylysine, arborols, dendrimers, and cyclodextrins. The advantages of using biomolecules include enhanced tissue targeting through specificity and delivery. Coupling of the chelating moieties to biomolecules can be accomplished by several known methods (e.g., Krejcarek and Tucker *Biochem. Biophys. Res. Comm*, 30 581 (1977); Hnatowich, et al. *Science*, 220, 613 (1983). For example, a reactive moiety present in one of the R groups is coupled with a second reactive group located on the biomolecule. Typically, a nucleophilic group is reacted with an electrophilic group to form a covalent bond between the biomolecule and the chelate. Examples of nucleophilic groups include amines, anilines, alcohols, phenols, thiols and hydrazines. Electrophilic group examples include halides, disulfides, epoxides, maleimides, acid chlorides, anhydrides, mixed anhydrides, activated esters, imidates, isocyanates and isothiocyanates. And finally, the compositions of the invention should provide the additional advantage of being kinetically inert.

Examples of suitable alkyl groups for use with the invention include methyl, ethyl, propyl, isopropyl, butyl, cyclohexyl, heptyl and octyl. Suitable alkoxy groups include methoxy, ethoxy, propoxy, butoxy, pentoxy, hexoxy, heptoxy and octoxy. Hydroxyalkyl groups suitable for use with the invention include both mono and poly hydroxyalkyls such as hydroxyethyl, 2-hydroxypropyl, 2,3-dihydroxypropyl, 2,3,4-trihydroxybutyl, tris(hydroxymethyl)methyl and 2-hydroxy-1-hydroxymethyl-ethyl. Suitable alkoxyalkyl groups include methoxymethyl, 2,3-dimethoxypropyl, tris (methoxymethyl)methyl, and 2-methoxy-1-methoxymethyl-ethyl.

Examples of suitable compounds of the invention are 1, 11-dimethyl-3, 9, 13, 19, 22, 28-hexaoxa-($N^6$, $N^6$, $N^{25}$-tricarboxymethyl)-6, 16, 25-triaza-bicyclo [9.9.9] nonacosane; 1-hydroxymethyl-13-(2-aminoethyl)-($N^3$, $N^{11}$, $N^{15}$, $N^{23}$, $N^{26}$, $N^{34}$-hexamethyl)-($N^7$, $N^{19}$, $N^{30}$-tricarboxymethyl)-3, 7, 11, 15, 19, 23, 26, 30, 34-nonaza-bicyclo [11.11.11]-penta triacontane HSA conjugate; 4, 10, 16, 22, 27, 33-hexaoxa-[$N^7$, $N^{19}$, $N^{30}$-(hydroxylamino) carboxymethyl]-1, 7, 13, 19, 30-pentaazabicyclo [11.11.11]-pentatriacontane; and 1-hydroxymethyl-11-carboxy-3, 9, 13, 19, 22, 28-hexathio-($N^6$, $N^{16}$, $N^{25}$-trisulfomethyl)-6, 16, 25-triaza-bicyclo [9.9.9] nonacosane poly-L-lysine conjugate.

Complexes of the novel ligands or compounds of the invention with one or more central metal ions or metal ion equivalents such as paramagnetic metals praseodymium(III), neodymium(III), samarium(III), ytterbium(III) terbium(III), dysprosium(III), holmium(III), erbium(III), iron(II), iron(III), manganese(II), manganese(III), gadolinium(III), chromium(III), cobalt(II) and nickel(II) are useful for enhancing magnetic resonance images. While such metal ions are themselves paramagnetic in nature and capable of altering the magnetic resonance signal characteristics of body tissues, organs or fluids, they may exhibit significant toxicity when administered in the form of ionic salts. However, novel complexes of the invention are relatively or substantially nontoxic and therefore useful for enhancing magnetic resonance images by favorably altering relaxation times $T_1$ and $T_2$ and affording improved contrast between normal and diseased tissues or organs.

The preferred complexes of the invention are those formed from the above ligands and iron(II), iron(III), manganese(II), manganese(III) and gadolinium(III) as the central metal ion or ions. Depending upon the particular ligand employed and the particular central metal ion used, the complexes formed may be neutral, ionic, cationic, or zwitterionic in nature, or they may be negatively charged. The neutral complexes are generally preferred and generally appear to exhibit relatively lower toxicity as compared to ionic or negatively charged complexes. The negatively charged complexes formed by the ligands and central metal ions enumerated above may be further complexed with one or more cations of an inorganic or organic base which are physiologically tolerated. Examples of cations for further complexing include sodium, potassium, calcium, and salts of N-methylglucamine, and diethanolamine.

Examples of preferred compounds of the invention and one or more central metal ions (i.e., complexes) include 1,11-dimethyl-3,9,13,19,22,28-hexaoxa-($N^6$, $N^{16}$, $N^{25}$-tricarboxymethyl)-6,16,25-triaza-bicyclo[9.9.9-]nonacosane, gadolinium(III) complex, 1-hydroxymethyl-13-(2-aminoethyl)-($N^3$, $N^{11}$, $N^{15}$, $N^{23}$, $N^{26}$, $N^{34}$-hexamethyl)-(N $N^7$,$N^{19}$, $N^{30}$-tricarboxymethyl)-3,7,11,15,19,23,26,30,34-nonaaza-bicyclo[11.11.11]-pentatriacontane, HSA conjugate, dysprosium(III) complex, 1-hydroxymethyl-13-(2-aminoethyl)-($N^3$, $N^{11}$, $N^{15}$, $N^{23}$, $N^{26}$, $N^{34}$-hexamethyyl)-N $^7$, $N^{19}$, $N^{30}$-tricarboxymethyl)-3,7,11,15,19,23,26,30,34-nonaaza-bicyclo[11.11.11]-pentatriacontane, HSA conjugate, ytterbium(III) complex, 4,10,16,22,27,33-hexaoxa-[$N^7$, $N^{19}$, $N^{30}$-(hydroxylamino)carboxymethyl]-1,7,13,19,30-pentaaza-bicyclo[11.11.11]-pentatriacontane, iron(HI) complex, 4,10,16,22,27,33-hexaoxa-[$N^7$, $N^{19}$, $N^{30}$-(hydroxylamino)carboxymethyl]-1,7,13,19,30-pentaaza-bicyclo[11.11.11]-pentatriacontane, ytterbium(III) complex, and 1-hydroxymethyl-11-carboxy-3,9,13,19,22,28-hexathio-($N^6$, $N^{16}$, $N^{25}$-trisulfomethyl)-6,16,25-triaza-bicyclo[9.9.9]nonacosane, poly-L-lysine conjugate, gadolinium(HI) complex.

In addition to their utility in magnetic resonance imaging procedures, the compositions of the invention can also be employed for delivery of either radiopharmaceuticals or heavy metals for x-ray contrast into the body. For use in diagnostic and therapeutic radiopharmaceuticals the complexed metal ion must be radioactive. Radioisotopes of the elements technetium, rhenium, indium, gallium, copper, yttrium, samarium and holmium are suitable. For use as X-ray contrast applications the complexed metal ion must be able to absorb adequate amounts of the X-rays. These metal ions are generally refered to as radioopaque. Suitable elements for use as the radioopaque metal ion include lead, bismuth, gadolinium, dysprosium, holmium and praseodymium.

Examples of preferred compounds for radiopharmaceuticals are 1,11-dimethyl-3,9,13,19,22,28-hexaoxa-($N^6$, $N^{16}$, $N^{25}$-tricarboxymethyl)-6,16,25-triazabicyclo[9.9.9-]nonacosane, gallium(HI) complex, 1,11-dimethyl-3,9,13,19,22,28-hexaoxa-($N^6$, $N^{16}$, $N^{25}$-tricarboxymethyl)-6,16,25-triazabicyclo[9.9.9-]nonacosane, yttrium(III) complex, 1-hydroxymethyl-13-(2-aminoethyl)-($N^3$, $N^{11}$, $N^{15}$, $N^{23}$, $N^{26}$, $N^{34}$-hexamethyl)-($N^{ 7}$, $N^{19}$, $N^{30}$-tricarboxymethyl)-3,7,11,15,19,23,26,30,34-nonaaza-bicyclo[11.11.11]-pentatriacontane, HSA conjugate, indium(III) complex, 1-hydroxymethyl-11-carboxy-3,9,13,19,22,28-hexathio-($N^6$, $N^{16}$, $N^{25}$-trisulfomethyl)-6,16,25-triaza-bicyclo[9.9.9]nonacosane, poly-L-lysine conjugate, technetium(V) complex, and 1-hydroxymethyl-11-carboxy-3,9,13,19,22,28-hexathio-($N^6$, $N^{16}$, $N^{25}$-trisulfomethyl)6,16,25-triaza-bicyclo[9.9.9]nonacosane, poly-L-lysine conjugate, rhenium(V) complex.

Examples of preferred compounds for x-ray contrast are 1,11-dimethyl-3,9,13,19,22,28-hexaoxa-($N^6$, $N^{16}$, $N^{25}$-tricarboxymethyl)-6,16,25-triazabicyclo[9.9.9-]nonacosane, bismuth(III) complex, 1-hydroxymethyl-13-(2-aminoethyl)-($N^3$, $N^{11}$, $N^5$, $N^{23}$, $N^{26}$, $N^{34}$-hexamethyl)-($N^{ 7}$, $N^{19}$, $N^{30}$-tricarboxymethyl)-3,7,11,15,19,23,26,30,34-nonaaza-bicyclo[11.11.11 ]pentatriacontane, HSA conjugate, holmium(III) complex, 4,10,16,22,27,33-hexaoxa-[$N^7$, $N^{19}$, $N^{30}$-(hydroxylamino)carboxymethyl]-1,7,13,19,20-pentaaza-bicyclo[ 11.11.11]-pentatriacontane, dysprosium(III) complex, 4,10,16,22,27,33-hexaoxa-[$N^7$, $N^{19}$, $N^{30}$-(hydroxylamino)carboxymethyl]-1,7,13,19,20-pentaaza-bicyclo[11.11.11]-pentatriacontane, bismuth(III) complex, and 1-hydroxymethyl-11-carboxy-3,9,13,19,22,28-hexathio-($N^6$, $N^{16}$, $N^{25}$-trisulfomethyl)6,16,25-triaza-bicyclo[9.9.9]nonacosane, poly-L-lysine conjugate, dysprosium(III) complex.

The compositions of the invention can be formulated into therapeutic or diagnostic compositions for enteral or parenteral administration. These compositions contain an effective amount of the paramagnetic ion complex along with conventional pharmaceutical carriers and excipients appropriate for the type of administration contemplated. For example, parenteral formulations advantageously contain a sterile aqueous solution or suspension of from about 0.05 to about 1.0M of a paramagnetic ion complex according to this invention. Parenteral compositions may be injected directly or mixed with a large volume parenteral composition for systemic administration. Preferred parenteral formulations have a concentration of paramagnetic ion complex of about 0.1M to about 0.5M. Such solutions also may contain pharmaceutically acceptable buffers and, optionally, electrolytes such as sodium chloride. The compositions may advantageously contain a slight excess (e.g., from about 0.01 to about 15.0 mole % excess) of a complexing agent or its complex with a physiologically acceptable, non-toxic cation. Such physiologically acceptable, non-toxic cations include calcium ions, magnesium ions, copper ions, zinc ions, salts of n-methylglucamine and diethanolamine, and the like. Generally, calcium ions are preferred.

Formulations for enteral administration may vary widely, as is well-known in the art. In general, such formulations are liquids which include an effective amount of the paramagnefic ion complex in aqueous solution or suspension. Such enteral compositions may optionally include buffers, surfactants, thixotropic agents, and the like. Compositions for oral administration may also contain flavoring agents and other ingredients for enhancing their organoleptic qualifies.

The diagnostic compositions are administered in doses effective to achieve the desired enhancement of the image. Such doses may vary widely, depending upon the particular paramagnetic ion complex employed, the organs or tissues which are the subject of the imaging procedure, the imaging procedure, the imaging equipment being used, and the like. In general, parenteral dosages will range from about 0.001 to about 1.0 mMol of paramagnetic ion complex per kg of patient body weight. Preferred parenteral dosages range from about 0.01 to about 0.5 mMol of paramagnetic ion complex per kg of patient body weight. Enteral dosages generally range from about 0.5 to about 100 mMol, preferably from about 1.0 to about 10 mMol, preferably from about 1.0 to about 20.0 mMol of paramagnetic ion complex per kg of patient body weight.

The diagnostic compositions of the invention are used in the conventional manner. The compositions may be administered to a patient, typically a warm-blooded animal, either systemically or locally to the organ or tissue to be imaged, and the patient then subjected to the imaging procedure. Protocols for imaging and instrument procedures are found in texts such as Stark, D. D.; Bradley, W. G. *Magnetic Resonance Imaging;* Mosby Year Book: St. Louis, Mo., 1992.

Radiopharmaceutical Imaging Procedures are found in Fred A. Mettler, Jr., M.D., M.P.H., Milton J. Guiberteau, M.D., *Essentials of Nuclear Medicine Imaging,* Grune and Stratton, Inc., New York, N.Y. 1983) and E. Edmund Kim, M.S., M.D. and Thomas P. Haynie, M.D., (MacMillan Publishing Co. Inc., New York, N.Y. 1987).

X-ray contrast Imaging Procedures are found in Albert A. Moss, M.D., Gordon Gamsu, M.D., and Harry K. Genant, M.D., *Computed Tomography of the Body,* (W. B. Saunders Company, Philadelphia, Pa. 1992) and M. Sovak, Editor, *Radiocontrast Agents,* (Springer-Verlag, Berlin 1984).

The following examples illustrate the specific embodiments of the invention described in this document. As would be apparent to skilled artisans, various changes and modifications are possible and are contemplated within the scope of the invention described.

EXAMPLES

Example 1

Synthesis of 1,11-dimethyl-3,9,13,19,22,28-hexaoxa-($N^6$, $N^{16}$, $N^{25}$-tricarboxymethyl)-6, 16,25-triaza bicyclo[9.9.9]nonacosane A solution of 2,2-dimethyl-5-hydroxymethyl-5-methyl-1,3-dioxane (13.4 g, 0.084 mol) in 630 mL of anhydrous tetrahydrofuran was cooled to −20° C. under argon atmosphere. Then a 0.5M solution of potassium bis(trimethylsilyl)amide in toluene (168 mL, 0.084 mol) was added and the mixture was stirred at −20° C. for 1 hr. The 2-benzyloxyethyltriflate (23.8 g, 0.084 mol) was added neat, keeping the temperature between −20° and −15° C. The resulting solution was stirred at this temperature for 1 hr, then gradually allowed to warm to 25° C. and stirred for 15 hrs. Dichloromethane (900 mL) was added and the solution was washed twice with 300 mL of water and once with 100 mL of saturated sodium chloride solution. The organic layer was dried over anhydrous sodium sulfate and evaporation of the solvents under reduced pressure gave 2,2-dimethyl-5-benzyloxyethoxymethyl-5-methyl-1,3-dioxane (24.6 g, 0.084 mol, 100%) which was not purified.

A solution of 2,2-dimethyl-5-benzyloxyethoxymethyl-5-methyl-1,3-dioxane (24.6 g, 0.084 mol) in 200 mL of 10% hydrochloric acid and 200 mL of tetrahydrofuran was stirred at 25° C. for 4 hrs. The pH of the mixture was adjusted to 7 with solid sodium bicarbonate and the aqueous solution was extracted several times with dichloromethane. The combined organic extracts were dried over anhydrous sodium sulfate and evaporated under reduced pressure to give 1-benzyloxyethoxymethyl-1,1-dihydroxymethylethane (18.4 g, 0.072 mol, 86%).

A solution of 1-benzyloxyethoxymethyl-1,1-dihydroxymethylethane (12.9 g, 0.051 mol) in 600 mL of anhydrous tetrahydrofuran was cooled to −20° C. under argon atmosphere. Then a 0.5M solution of potassium bis(trimethylsilyl)amide in toluene (218 mL, 0.109 mol) was added and the mixture was stirred for 1 hr. The 2-benzyloxyethyltriflate (30.9 g, 0.109 mol) was added neat keeping the temperature between −20° C. and −15° C. After the addition was complete, the mixture was allowed to gradually warm to 25° C. and was stirred for 15 hrs. Dichloromethane (1 L) was added to the reaction mixture and the resulting solution was washed with 1 L of water, dried over anhydrous sodium sulfate and evaporated under reduced pressure to give crude 1,1,1-tris(benzyloxyethoxymethyl)ethane. This mixture was chromatographed over silica gel using an ethyl acetate/hexane gradient to obtain pure 1,1,1-tris(benzyloxyethoxymethyl) ethane (13.9 g, 0.027 mol, 53%).

A mixture of 1,1,1-tris(benzyloxyethoxymethyl)ethane (13.9 g, 0.027 mol) and palladium hydroxide on carbon, Pd content 20% (2.8 g) in 100 mL of methanol was hydrogenated at 50 psi in a Parr apparatus for 4 hrs. The catalyst was removed by filtration through Celite and the filtrate was evaporated under reduced pressure to give 1,1,1-tris(hydroxyethoxymethyl)ethane (6.7 g, 0.026 mol, 99%).

A solution of 1,1,1-tris(hydroxyethoxymethyl)ethane (6.7 g, 0.026 mol) in 35 mL of anhydrous pyridine was cooled to −10° C. Then solid p-toluenesulfonyl chloride (16.6 g, 0.087 mol) was added in portions over 1.5 hrs. The mixture was kept at −10° C. for 15 hrs. The resulting slurry was partitioned between dichloromethane (100 mL) and water (50 mL) and the layers were separated. The organic layer was washed with water (50 mL), dried over anhydrous sodium sulfate and evaporated to give a crude gum. This material was purified over silica gel using 1% methanol/dichloromethane as eluant to give 1,1,1-tris(tosylethoxymethyl)ethane (8.9 g, 0.013 mol, 47%).

A slurry of 1,1,1-tris(tosylethoxymethyl)ethane (4.5 g, 6.30 mmol) and potassium phthalimide (3.5 g, 18.90 mmol) in 45 mL of N,N-dimethylacetamide was heated at 80°–85 ° C. for 15 hrs. The solvent was removed under reduced pressure and the residue was partitioned between dichloromethane and water. The layers were separated and the organic layer was washed with water, dried over anhydrous sodium sulfate and evaporated to give 1,1,1-tris(phthalimidoethoxymethyl)ethane (4.0 g, 6.30 mmol, 100%).

A solution of 1,1,1-tris(phthalimidoethoxymethyl)ethane (4.0 g, 6.30 mmol) in 100 mL of absolute ethanol was heated to 50C. Then a 55% solution of hydrazine hydrate (3.7 mL, 63.00 mmol) was added dropwise and the resulting mixture was heated at 50° C. for 5 hrs. The reaction was cooled to 25° C. and the solids were filtered. The filtrate was evaporated to give an oil which was purified over reversed phase packing (C-18) using a methanol/water gradient as eluant to yield 1,1,1-tris-(aminoethoxymethyl)ethane (1.3 g, 5.22 mmol, 83 % ).

To a solution of 1,1,1-tris(aminoethoxymethyl)ethane (1.1 g, 4.40 mmol) in 10 mL of pyridine was added p-toluenesulfonylchloride (2.5 g, 13.2 mmol) in portions over 1 hr. The mixture was stirred at 25—C for 15 hrs. Dichloromethane (100 mL) and water (50 mL) were added to the reaction and the layers were separated. The organic layer was washed three times with 100 mL of 10% hydrochloric acid solution, once with saturated sodium bicarbonate solution (50 mL), dried over anhydrous sodium sulfate and evaporated under reduced pressure. The crude oil was purified by chromatography over silica gel using an ethyl acetate/hexane gradient as eluant to yield 1,1,1-tris(tosylamidoethoxymethyl)ethane (1.2 g, 1.69 mmol, 40%).

A mixture of 1,1,1-tris(tosylethoxymethyl)ethane (1.2 g, 1.69 mmol), 1,1,1-tris(tosylamidoethoxymethyl)ethane (1.2 g, 1.69 mmol) and anhydrous potassium carbonate,
−325 mesh (0.7 g, 5.1 mmol) in 100 mL of anhydrous N,N-dimethylacetamide was heated at 80°–85° C. under argon atmosphere for 15 hrs. The solvent was removed under reduced pressure and the residue was partitioned between dichloromethane (100 mL) and water (50 mL). The layers were separated and the organic layer was dried over anhydrous sodium sulfate and evaporated to give a gum. This material was chromatographed over silica gel using an ethyl acetate/hexane gradient as eluant to give 1,11-dimethyl-3,9,13,19,22,28-hexaoxa-($N^6$, $N^{16}$, $N^{25}$-tritosylamido)-6,16,25-triaza-bicyclo[9.9.9-]nonacosane (0.34 g, 0.37 mmol, 22%).

A solution of 1,11-dimethyl-3,9, 13,19,22,28-hexaoxa-($N^6$, $N^{16}$, $N^{25}$-tritosylamido)-6,16, 25-triaza-bicyclo[9.9.9]nonacosane (0.08 g, 0.09 mmol) in 3 mL of tetrahydrofuran was added to liquid ammonia (10 mL) in a dry ice/isopropanol bath. Sodium pellets were added as needed to maintain a dark blue color. The bath was removed and the solution was allowed to reflux for 30 min. Then solid ammonium chloride was added to decolorize the solution and the solvents were allowed to evaporate. The residue was triturated with methanol and the solvents were evaporated. The oil was dissolved in water and purified through reversed phase packing (ODS) using a methanol/water gradient as eluant to give 1,11-dimethyl-3,9,13,19,22,28-hexaoxa-6,16,25-triaza-bicyclo[9.9.9]nonacosane (0.01 g, 0.02 mmol, 25%).

A mixture of 1,11-dimethyl-3,9,13,19,22,28-hexaoxa-6,16,25-triazabicyclo[9.9.9]nonacosane (10.0 mg, 0.02 mmol), t-butylbromoacetate (12.0 mg, 0.06 mmol), and diisopropylethylamine (8.0 mg, 0.06 mmol) in 2 mL of anhydrous acetonitrile was heated at 50° C. for 15 hrs. The solvents were removed under reduced pressure and the residue was partitioned between dichloromethane (50 mL) and water (10 mL). The layers were separated and the organic layer was dried over anhydrous sodium sulfate and evaporated to give 1,11-dimethyl-3,9,13,19,22,28-hexaoxa-[$N^6$, $N^{16}$, $N^{25}$-tri(t-butoxycarbonylmethyl) ]-6,16,25-triaza-bicyclo[9.9.9]nonacosane (14.0 mg, 0.02 mmol, 88%).

To a solution of 1,11-dimethyl-3,9,13,19,22,28-hexaoxa-[$N^6$, $N^{16}$, $N^{25}$-tri(t-butoxycarbonylmethyl) ]-6,16,25-triaza-bicyclo[9.9.9]nonacosane (14.0 mg, 0.02 mmol) in 2 mL of dichloromethane is added trifluoroacetic acid (0.50 mL). The solution is stirred at 25° C. for 15 hrs. The solvents are removed under reduced pressure and the residue is dissolved in water. The pH of the aqueous solution is adjusted to 7 with ammonium hydroxide and the solution is chromatographed over reversed phase packing (ODS) using water as eluant to give 1,11-dimethyl-3,9,13,19,22,28-hexaoxa-($N^6$, $N^{16}$ $N^{25}$-tricarboxymethyl)-6,16,25-triaza-bicyclo[9.9.9]nonacosane (12.0 mg, 0.02 mmol, 100% ).

Example 2

Synthesis of 1,11-dimethyl-3,9,13,19,22,28-hexaoxa-($N^6$, $N^{16}$, $N^{25}$-tricarboxymethyl)-6,16,25-triaza-bicyclo[9.9.9]nonacosane, gadolinium(III) complex.

To a solution of 1,11-dimethyl-3,9,13,19,22,28-hexaoxa-($N^6$, $N^{16}$, $N^{25}$-tricarboxymethyl)-6,16,25-triaza-bicyclo[9.9.9]nonacosane (12.0 mg, 0.02 mmol) in 1 mL of deionized water is added gadolinium oxide (3.6 mg, 0.01 mmol). The mixture is heated at 80° C. under argon atmosphere for 15 hrs. The resulting solution is filtered and the filtrate is evaporated to give 1,11-dimethyl-3,9,13,19,22,28-hexaoxa-($N^6$, $N^{16}$, $N^{25}$-tricarboxymethyl)-6,16,25-triaza-bicyclo[9.9.9]nonacosane, gadolinium(III) complex (12.4 mg, 0.02 mmol, 100% ).

Example 3

Synthesis of 1-hydroxymethyl- 11-carboxy-3,9,13,19,22,28-hexathio-($N^6$, $N^{16}$, $N^{25}$-trisulfomethyl)-6,16,25-triaza-bicyclo[9.9.9]nonacosane, poly-L-lysine conjugate To a suspension of pentaerythritol (13.6 g, 0.100 mol) in 10 mL of toluene was added freshly distilled triethyl orthoacetate (16.2 g. 18.3 mL, 0.100 mol) and p-toluenesulfonic acid monohydrate (50 mg). The mixture was slowly heated in an oil bath and ethanol was distilled from the mixture over a period of 12 hrs. After removal of the ethanol, the bath temperature was raised to 125° C. and toluene was distilled off until the solution was homogeneous (about 30 mL). The residue was sublimed (bulb to bulb, ~130$_{-C}$, 2.5 mmHg) to give 4-(hydroxymethyl)-1-methyl-2,6,7-trioxabicyclo[2.2.2]octane (15.0 g, 0.093 mol, 93%).

Powdered potassium hydroxide (16.2 g, 0.290 mol) is suspended in 100 mL of dimethyl sulfoxide and the mixture is stirred at 25° C. for 5 min. Then 4-(hydroxymethyl)-1-methyl-2,6,7-trioxabicyclo[2.2.2]octane (10.0 g, 0.062 mol) is added followed by bromomethyl methyl ether (9.3 g, 6.1 mL, 0.074 mol). The reaction mixture is stirred for 30 min and then diluted with water (1 L) and extracted with dichloromethane several times. The combined organic layers are washed with saturated sodium chloride (100 mL), dried over anhydrous sodium sulfate and evaporated under reduced pressure to give 4-(methoxy)-1-methyl-2,6,7-trioxabicyclo[2.2.2]octane. This crude material is dissolved in methanol (100 mL) and stirred with pyridinium p-toluenesulfonate (1.6 g, 6.200 mmol) in water (100 mL) for 30 min. The pH of the solution is adjusted to 7 with solid sodium bicarbonate and the solvents are removed under reduced pressure. The resulting solids are triturated with methanol and the methanol solution is evaporated to give 2-(methoxymethoxy)-1,1,1-tris(hydroxymethyl)ethane.

A solution of 2-(methoxymethoxy)-1,1,1-(hydroxymethyl)ethane (10.6 g, 0.059 mol) in 50 mL of pyridine is cooled to 0° C. and p-toluenesulfonyl chloride (37.1 g, 0.195 mol) is added in portions over 30 min. The solution is kept at 0° C. for 15 hrs and then partitioned between dichloromethane (200 mL) and water (100 mL). The layers are separated and the organic solution is washed twice with 200 mL of water. The organic layer is dried over anhydrous sodium sulfate and evaporated under reduced pressure to give 2-(methoxymethoxy)-1,1,1-tris-(tosylmethyl)ethane.

A mixture of 2-(methoxymethoxy)-1,1,1-tris-(tosylmethyl)ethane (26.9 g, 0.042 mol) and potassium thioacetate (15.8 g, 0.139 mol) in 100 mL of absolute ethanol is heated at reflux for 8 hrs. The solvents are removed under reduced pressure and the residue is partitioned between dichloromethane (200 mL) and water (100 mL). The organic layer is dried over anhydrous sodium sulfate and evaporated to give 2-(methoxy)-1,1,1-tris(thioacetylmethyl)ethane. This crude material is dissolved in 100 mL of methanol and stirred with 100 mL of 10% sodium hydroxide solution at 25° C. for 2 hrs. The solvents are removed under reduced pressure and the solids are triturated with methanol. The combined methanol solutions are evaporated to give 2-(methoxymethoxy)-1,1,1-tris( thiomethyl)ethane.

A mixture of 2-(methoxymethoxy)-1,1,1-tris-(thiomethyl)ethane (8.2 g, 0.036 mol), potassium carbonate (14.9 g, 0.108 mol) and N-tosylaziridine (21.3 g, 0.108 mol) in 50 mL of N,N-dimethylacetamide is heated at 80° C. for 15 hrs. Dichloromethane (200 mL ) is added and the mixture is washed with water (100 mL). The organic solution is dried over anhydrous sodium sulfate and evaporated under reduced pressure to give 2-(methoxymethoxy)-1,1,1-tris-[[2-(N-tosylamido )ethyl]-thiomethyl]ethane.

To a solution of 4-(hydroxymethyl)-1-methyl-2,6,7-trioxabicyclo[2.2.2]octane (10.0 g, 0.062 mol) in 200 mL of acetone is added Jones reagent (chromium trioxide and sulfuric acid) until an orange color persisted. The excess oxidant is removed by the addition of 2-propanol until a green color is obtained and the solvents are evaporated under reduced pressure. The residue is partitioned between dichloromethane (100 mL) and water (50 mL) and the layers are separated. The organic layer is washed with water, dried over anhydrous sodium sulfate and evaporated under reduced pressure to give 4-carboxy-1-methyl-2,6,7-trioxabicyclo[2.2.2]octane.

A mixture of 4-carboxy-1-methyl-2,6,7-trioxabicyclo[2.2.2]octane (9.3 g, 0.053 mol) and 1,3-dicyclohexylcarbodiimide (10.9 g, 0,053 mol) in 100 mL of acetonitrile is stirred at 25° C. for 30 min. Then 2-methyl-2-propanol (3.9 g, 5.0 mL, 0.053 mol) is added and the resulting mixture is stirred for 15 hrs. The solids are filtered and the filtrate is evaporated under reduced pressure to yield 4-(t-butoxycarbonyl)-1-methyl-2,6,7-trioxabicyclo[2.2.2]octane as a crude oil. This material is dissolved in 100 mL of tetrahydrofuran and stirred with 50 mL of 10% hydrochloric acid for 1 hr. The pH of the solution is adjusted to 7 with solid sodium bicarbonate and the solvents are removed under reduced pressure. The solids are triturated with methanol and the combined methanol solutions are evaporated to give t-butyl-tris(hydroxymethyl)acetate.

A solution of t-butyl-tris(hydroxymethyl)acetate (9.9 g, 0.048 mol) in 50 mL of pyridine is cooled to 0° C. and then portions of p-toluenesulfonyl chloride (30.1 g, 0.158 mol) are added over 1 hr. The mixture is kept at 0° C. for 15 hrs. Then dichloromethane (200 mL) is added and the solution is washed four times with 100 mL of 10% hydrochloric acid, once with 100 mL of saturated sodium bicarbonate and once with 100 mL of saturated sodium chloride. The organic layer is dried over anhydrous sodium sulfate and evaporated under reduced pressure to give t-butyl-tris(tosylmethyl)acetate.

Sodium hydride (2.6 g, 0.108 mol) is added slowly to a solution of 2-benzyloxyethanethiol (18.1 g, 0.108 mol) in 200 mL of anhydrous tetrahydrofuran. The slurry is stirred at 25° C. for 30 min. and then a solution of t-butyl-tris(tosylmethyl)acetate (23.7 g, 0.036 mol) in 100 mL of anhydrous tetrahydrofuran is added dropwise. After the addition is complete, the mixture is heated at 80° C. for 15 hrs. The reaction mixture is cooled to 25° C. and water (50 mL) is slowly added. Then the solution is extracted several times with dichloromethane and the combined extracts are dried over anhydrous sodium sulfate and evaporated under reduced pressure to give t-butyl-tris[[(2-benzyloxy)ethyl]thiomethyl]acetate.

A slurry of t-butyl-tris[[(2-benzyloxy)ethyl]thiomethyl]acetate (19.0 g, 0.029 mol) and palladium hydroxide on carbon (0.4 g, 20% palladium) in 200 mL of methanol is hydrogenated at 50 psi using a Parr hydrogenation apparatus. After 4 hrs., the catalyst is removed by filtration through Celite and the tiltrate is evaporated under reduced pressure to give t-butyl-tris[(2-hydroxyethyl)-thiomethyl]acetate.

A solution of t-butyl-tris[(2-hydroxyethyl)thiomethyl]acetate (11.2 g, 0.029 mol) in 50 mL of pyridine is cooled to 0° C. and p-toluenesulfonyl chloride (18.3 g, 0.096 mol) is added in portions over 1 hr. The mixture is kept at 0° C. for 15 hrs. Then dichloromethane (200 mL) is added and the solution is washed four times with 100 mL of 10% hydrochloric acid, once with 100 mL of saturated sodium bicarbonate and once with 100 mL of water. The organic layer is dried over anhydrous sodium sulfate and evaporated to give t-butyl-tris[(2-tosylethyl)-thiomethyl]acetate.

A mixture of t-butyl-tris[(2-tosylethyl)thiomethyl]acetate (10.0 g, 0.013 mol), 2-(methoxymethoxymethyl)-1,1,1-tris[[2-(N-tosylamido)ethyl]thiomethyl]ethane (9.4 g, 0.013 mol) and potassium carbonate (5.4 g, 0.039 mol) in 1 L of anhydrous N,N-dimethylacetamide is heated at 80° C. under argon atmosphere for 15 hrs. The solvents are removed under reduced pressure and the residue is partitioned between dichloromethane (200 mL) and water (100 mL). The layers are separated and the organic layer is dried over anhydrous sodium sulfate and evaporated to give 1-(methoxymethoxymethyl)-11-t-butoxycarbonyl-3,9,13, 19,22,28-hexathio-($N^6$, $N^{16}$, $N^{25}$-tritosylamido )-6,16,25-triazabicyclo[9.9.9]nonacosane.

A solution of 1-(methoxymethoxymethyl)-11-t-butoxycarbonyl-3,9,13,19,22,28-hexathio(N, N,N-tritosylamido)-6,16,25-triaza-bicyclo[9.9.9]-nonacosane (4.5 g, 3.900 mmol) in 20 ml of tetrahydrofuran is added to liquid ammonia (100 mL) in a dry ice/2-propanol bath. Sodium pellets are added as needed to maintain a dark blue color. The bath is removed and the solution is allowed to stir at refluxing ammonia for 30 min. Then solid ammonium chloride is added to decolorize the reaction solution and the solvents are evaporated. The residue is triturated with methanol and the combined solutions are evaporated to give 1-(methoxymethoxymethyl)-11-t-butoxycarbonyl-3,9, 13,19,22,28-hexathio-6, 16,25-triaza-bicyclo[9.9.9]nonacosane.

A solution of 1-(methoxymethoxy)methyl-11-t-butoxycarbonyl-3,9,13,19,22,28-hexathio-6,16,25-triaza-bicyclo[9.9.9]nonacosane (2.0 g, 3.12 mmol) in 20 mL of tetrahydrofuran and 20 mL of water is adjusted to pH 10 with 1N sodium hydroxide. Then chloromethylsulfonic acid (1.2 g, 9.36 mmol) is added and the mixture is stirred at 25$_{-C for}$ 15 hrs., keeping the pH between 9 and 10 with 1N sodium hydroxide. The pH of the solution is brought to 12 with 1N sodium hydroxide and the solution was heated at 100$_{-C for}$ 1 hr. The water is evaporated under reduced pressure to give 1-(methoxymethoxymethyl)-11-carboxy-3,9,13,19,22,28-hexathio-($N^6$, $N^{16}$, $N^{25}$-trisulfomethyl)-6,16,25-triazabicyclo[9.9.9-]nonacosane. A mixture of 1-(methoxymethoxymethyl)-11-carboxy-3,9,13,19,22,28-hexathio-($N^6$, $N^{16}$, $N^{25}$-trisulfomethyl)-6,16,25-triabicyclo-[9.9.9]nonacosane (1.0g, 1.15mmol), 1,3-dicyclohexylcarbodiimide (0.24g, 1.15mmol) and N-hydroxysuccinimide (0.13g, 1.15mmol) in 20 mL of acetonitrile is stirred at 25° C. for 15 hrs. The solid is filtered and the tiltrate is added in portions to a sodium bicarbonate buffer solution (pH 8) of poly-L-lysine, molecular weight 1000–4000 (0.92g, 0.23mmol). After 15 hrs. at 25° C. the solution of 1-(methoxymethoxymethyl)- 11-carboxy-3,9, 13, 19,22,28-hexathio-($N^6$,$N^{16}$, $N^{25}$-trisulfomethyl)-6,16,25-triazabicyclo[9.9.9]nonacosane, poly-L-lysine conjugate, is used to make the dysprosium complex of Example 4.

Example 4

Synthesis of 1-hydroxymethyl-11-carboxy-3,9,13,19,22,28-hexathio-($N^6$, $N^{16}$, $N^{25}$-trisulfomethyl)-6,16,25-triazabicyclo[9.9.9]nonacosane, poly-L-lysine conjugate, dysprosium(III) complex.

Dysprosium oxide (0.21 g, 0.56 mmol) is added to a solution of 1-(methoxymethoxymethyl)-11-carboxy-3,9,13,19,22,28-hexathio-($N^6$, $N^{16}$, $N^{25}$-trisulfomethyl)-6,16,25-triazabicyclo-[9.9.9]nonacosane, poly-L-lysine conjugate, prepared in Example 3. The mixture is stirred for 15 hrs and then the pH is adjusted to 4 with 0.1N hydrochloric acid. After 1 hr the solution is purified through a phosphate buffered Sephadex G-50 gel-filtration column to give 1-hydroxymethyl-11-carboxy-3,9,13,19,22,28-hexathio-($N^6$, $N^{16}$, $N^{25}$-trisulfomethyl)-6,16,25-triazabicyclo[9.9.9]nonacosane, poly-L-lysine conjugate, dysprosium(III) complex.

Although the invention has been described with respect to specific modifications, the details thereof are not to be construed as limitations, for it will be apparent that various equivalents, changes and modifications may be resorted to without departing from the spirit and scope thereof, and it is understood that such equivalent embodiments are to be included therein.

What is claimed is:

1. A compound of the general formula:

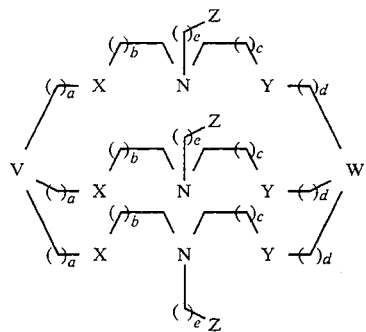

Wherein V is $CR_1$; W is $CR_2$ or N; $R_1$ and $R_2$ may be the same or different and are hydrogen, $C_1$-$C_8$ alkyl, or $C_6$-$C_{10}$ aryl, optionally $R_1$ and $R_2$ may be substituted by one or more hydroxy, $C_1$-$C_8$ alkyl, $C_1$-$C_8$ hydroxyalkyl, $C_1$-$C_8$ alkoxy, $C_6$-$C_{10}$ aryl, $C_6$-$C_{10}$ hydroxyaryl, $C_6$-$C_{10}$ aryloxy, $-CO_2R_3$, $CONR_4R_5$, or $-NR_4R_5$; X and Y may be the same or different and the O, $NR_6$, or S; $R_3$, $R_4$, $R_5$, and $R_6$, may be the same or different and are hydrogen, $C_1$-$C_8$ alkyl, $C_1$-$C_8$ hydroxyalkyl, or $C_1$-$C_8$ alkoxyalkyl; $R_4$ and $R_5$ may form a 5 or 6 membered carbocyclic ring; a, b, c, d and e may be same or different and are zero to about 10; and Z is $-CO_2H$, $-PO_3H_2$, $-SO_3H$, or $-CONHOH$.

2. The compound of claim 1 wherein V is $CR_1$; $R_1$ is $CH_3$; W is $CR_2$; $R_2$ is $CH_3$; X is O; Y is O; a is 1, b is 1; c is 1; d is 1; e is 1; and z is $CO_2H$.

3. A compound of the general formula:

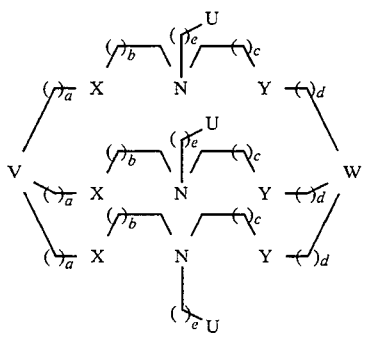

Wherein V is $CR_1$; W is $CR_2$ or N; $R_1$ and $R_2$ may be the same or different and are hydrogen, $C_1$-$C_8$ alkyl, or $C_6$-$C_{10}$ aryl, optionally $R_1$ and $R_2$ may be substituted by one or more hydroxy, $C_1$-$C_8$ alkyl, $C_1$-$C_8$ hydroxyalkyl, $C_1$-$C_8$ alkoxy, $C_6$-$C_{10}$ aryl, $C_6$-$C_{10}$ hydroxyaryl, $C_6$-$C_{10}$ aryloxy, $-CO_2R_3$, $CONR_4R_5$, or $-NR_4R_5$; X and Y may be the same or different and the O, $NR_6$, or S; $R_3$, $R_4$, $R_5$, and $R_6$, may be the same or different and are hydrogen, $C_1$-$C_8$ alkyl, $C_1$-$C_8$ hydroxyalkyl, or $C_1$-$C_8$ alkoxyalkyl; $R_4$ and $R_5$ may form a 5 or 6 membered carbocyclic ring; a, b, c, d and e may be same or different and are zero to about 10; U is $-CO_2M$, $-PO_3HM$, $-SO_3M$ or $CONHOM$; and M is a metal ion or equivalent and/or a physiologically acceptable cation of an inorganic or organic base.

4. The compound of claim 3 wherein V is $CR_1$; $R_1$ is $CH_3$; W is $CR_2$; $R_2$ is $CH_3$; X is O; Y is O; a is 1; b is 1; c is 1; d is 1; e is 1; U is $CO_2M$; and M is gadolinium.

5. The compound of claim 3 wherein V is $CR_1$; $R_1$ is $CH_3$; W is $CR_2$; $R_2$ is $CH_3$; X is O; Y is O; a is 1; b is 1; c is 1; d is 1; e is 1; U is $CO_2M$; and M is bismuth.

6. The compound of claim 3 wherein V is $CR_1$; $R_1$ is $CH_3$; W is $CR_2$; $R_2$ is methyl; X is O; Y is O; a is 1; b is 1; c is 1; d is 1; e is 1; U is $CO_2M$; and M is gallium.

7. The compound of claim 3 wherein V is $CR_1$; $R_1$ is $CH_3$; W is $CR_2$; $R_2$ is $CH_3$; X is O; Y is O; a is 1; b is 1; c is 1; d is 1; e is 1; U is $CO_2M$; and M is yttrium.

8. A method of imaging comprising administering to a patient a compound of the general formula:

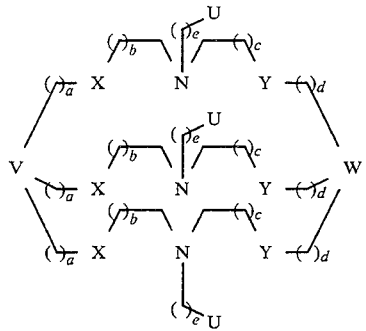

Wherein V is $CR_1$; W is $CR_2$ or N; $R_1$ and $R_2$ may be the same or different and are hydrogen, $C_1$-$C_8$ alkyl, or $C_6$-$C_{10}$ aryl, optionally $R_1$ and $R_2$ may be substituted by one or more hydroxy, $C_1$-$C_8$ alkyl, $C_1$-$C_8$ hydroxyalkyl, $C_1$-$C_8$ alkoxy, $C_6$-$C_{10}$ aryl, $C_6$-$C_{10}$ hydroxyaryl, $C_6$-$C_{10}$ aryloxy, $-CO_2R_3$, $CONR_4R_5$, or $-NR_4R_5$; X and Y may be the same or different and are O, $NR_6$, or S; $R_3$, $R_4$, $R_5$, and $R_6$, may be the same or different and are hydrogen, $C_1$-$C_8$ alkyl, $C_1$-$C_8$ hydroxyalkyl or $C_1$-$C_8$ alkoxyalkyl; $R_4$ and $R_5$ may form a 5 or 6 membered carbocyclic ring; a, b, c, d and e may be the same or different and are zero to about 10; U is $-CO_2M$, $-PO_3HM$, $-SO_3M$ or $CONHOM$; and M is a metal ion or equivalent and/or a physiologically acceptable cation of an inorganic or organic base and performing a diagnostic imaging procedure upon said patient.

9. The method of claim 8 wherein V is $CR_1$; $R_1$ is $CH_3$; W is $CR_2$; $R_2$ is $CH_3$; X is O; Y is O; a is 1; b is 1; c is 1; d is 1; e is 1; U is $CO_2M$; and M is gadolinium.

10. The method of claim 8 wherein V is $CR_1$; $R_1$ is $CH_3$; W is $CR_2$; $R_2$ is $CH_3$; X is O; Y is O; a is 1; b is 1; c is 1; d is 1; e is 1; U is $CO_2M$; and M is bismuth.

11. The method of claim 8 wherein V is $CR_1$; $R_1$ is $CH_3$; W is $CR_2$; $R_2$ is methyl; X is O; Y is O; a is 1; b is 1; c is 1; d is 1; e is 1; U is $CO_2M$; and M is gallium.

12. The method of claim 8 wherein V is $CR_1$; $R_1$ is $CH_3$; W is $CR_1$; $R_2$ is $CH_3$; X is O; Y is O; a is 1; b is 1; c is 1; d is 1; e is 1; U is $CO_2M$; and M is yttrium.

* * * * *